United States Patent
Haese et al.

(10) Patent No.: US 7,126,033 B2
(45) Date of Patent: Oct. 24, 2006

(54) METHOD FOR ISOMERIZING ALLYL ALCOHOLS

(75) Inventors: Frank Haese, Lambsheim (DE); Klaus Ebel, Lampertheim (DE); Kirsten Burkart, Ludwigshafen (DE); Signe Unverricht, Mannheim (DE); Peter Münster, Römerberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 14 days.

(21) Appl. No.: 10/497,524

(22) PCT Filed: Dec. 4, 2002

(86) PCT No.: PCT/EP02/13689

§ 371 (c)(1),
(2), (4) Date: Jun. 3, 2004

(87) PCT Pub. No.: WO03/048091

PCT Pub. Date: Jun. 12, 2003

(65) Prior Publication Data

US 2005/0070745 A1    Mar. 31, 2005

(30) Foreign Application Priority Data

Dec. 7, 2001 (DE) ................. 101 60 146

(51) Int. Cl.
*C07C 35/00* (2006.01)
*C07C 27/00* (2006.01)
(52) U.S. Cl. ...................... 568/875; 568/906
(58) Field of Classification Search ............... 568/875, 568/906
See application file for complete search history.

(56) References Cited

U.S. PATENT DOCUMENTS

| 4,465,787 A | 8/1984 | Horner et al. |
| 4,536,347 A | 8/1985 | Horner et al. |
| 5,998,680 A | 12/1999 | Kiefer et al. |
| 6,566,564 B1 * | 5/2003 | Ebel et al. ............ 568/875 |
| 2004/0097765 A1 * | 5/2004 | Haese et al. ............ 568/906 |

FOREIGN PATENT DOCUMENTS

| DE | 25 16 698 | 10/1975 |
| DE | 197 07 385 | 8/1998 |
| DE | 197 38 083 | 3/1999 |
| DE | 199 58 603 | 6/2001 |
| DE | 100 46 865 | 3/2002 |
| EP | 0 071 787 | 2/1983 |
| EP | 0 860 415 | 8/1998 |
| WO | WO 00/42177 | 6/2001 |

OTHER PUBLICATIONS

Hosogai et al, "Selective allylic rearrangement with tungsten catalyst" Chemistry Letters pp. 357-360, 1982 Chemical Society of Japan.*

* cited by examiner

*Primary Examiner*—Samuel Barts
*Assistant Examiner*—Lalitha Nagubandi
(74) *Attorney, Agent, or Firm*—Novak Druce & Quigg, LLP

(57) ABSTRACT

The present invention relates to a process for isomerizing reactant allyl alcohols to product allyl alcohols in the presence of a catalyst, wherein the reactant allyl alcohol is rearranged to product allyl alcohol in semicontinuous or continuous mode in a catalyst-containing suitable reactor. In particular, the process according to the invention is used to prepare linalool from Geraniol and/or nerol.

12 Claims, No Drawings

METHOD FOR ISOMERIZING ALLYL ALCOHOLS

The present invention relates to a process for isomerizing reactant allyl alcohols to product allyl alcohols in the presence of a catalyst, wherein the reactant allyl alcohol is rearranged to product allyl alcohol in semicontinuous or continuous mode in a catalyst-containing suitable reactor. In particular, the process according to the invention is used to prepare linalool from geraniol and/or nerol.

Allyl alcohols are important intermediates in industrial organic product synthesis. Tertiary allyl alcohols in particular serve, for example, as intermediates in the preparation of scents or else as additives in soaps and detergents.

Allyl alcohols isomerize under acidic catalysis. This isomerization corresponds to a 1,3-migration of the hydroxyl group and an internal shift of the double bond, as shown in the following equation with the general formulae I and II:

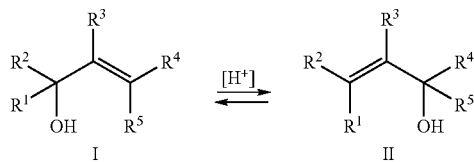

In which the $R^1$ to $R^5$ radicals are each hydrogen or a mono- or polyunsaturated or saturated $C_1$–$C_{12}$-alkyl radical which may optionally be substituted.

Geraniol (2-trans-3,7-dimethyl-2,6-octadien-8-ol), nerol (2-cis-3,7-dimethyl-2,6-octadien-8-ol) and 2-linalool (3,7-dimethyl-1,6-octadien-3-ol) are important compounds in the scents industry. They are either used directly as scents or converted to high molecular weight scents by reacting with other compounds. These terpene alcohols are also important as $C_{10}$ building blocks in the synthesis of vitamins such as vitamin E and vitamin A.

The isomerization reactions of allyl alcohols with acids were initially carried out using acids as catalysts. However, these processes were only of limited importance, since they were dominated by side reactions, for example dehydrations or cyclizations.

For the rearrangement of reactant allyl alcohols to product allyl alcohols, in particular for the rearrangement of geraniol or nerol or geraniol/nerol mixtures to linalool, the prior art describes batchwise processes.

DE 25 16 698 describes a batchwise process for rearranging geraniol and/or nerol to linalool, in which the reactant is initially charged, the catalyst is added, then the equilibrium is established and subsequently the linalool formed is distilled out of the reaction mixture.

A disadvantage of the procedure described is that the rearrangement has to be interrupted very frequently, in order to remove high boilers which occur in the bottom and to meter in fresh catalyst.

The complicated batchwise discontinuous reaction control results in long reaction times and also, for the industrial scale, unsatisfactory yields.

In addition, all processes described in the prior art start from isolated reactant allyl alcohol which has been freed of by-products by purification.

When the preparation of linalool starts, for example, directly from nerol and/or geraniol obtained from the citral hydrogenation, the by-products obtained in the citral hydrogenation also have to be taken into account in the reaction control. This by-product spectrum has consequences for the rearrangement to linalool.

The citral hydrogenation in batchwise mode is described, for example, in EP 71787.

It is an object of the present invention to develop a process for isomerizing reactant allyl alcohols to product allyl alcohols, in particular for the isomerization of geraniol/nerol to linalool, which firstly does not have the disadvantages of the batchwise process and secondly, even starting from the reactants which have not been freed of by-products by purification, leads to an economically viable process having good space-time yields.

We have found that this object is achieved by a process for isomerizing reactant allyl alcohols of the general formula (I) to product allyl alcohols of the general formula (II)

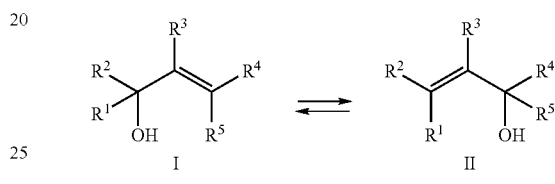

where R1 to R5 are each hydrogen or a mono- or polyunsaturated or saturated $C_1$–$C_{12}$-alkyl which may optionally be substituted, wherein at least one reactant allyl alcohol or mixtures thereof is rearranged in continuous or semicontinuous mode to give the corresponding product allyl alcohol, by simultaneously metering in at least one reactant allyl alcohol or mixtures thereof into a catalyst-containing suitable reactor.

Preference is given to simultaneously distilling off the product allyl alcohol formed.

Allyl alcohols of the general formula (I) or (II) which can advantageously be isomerized with the aid of the process according to the invention include: 2-methyl-3-buten-2-ol, prenol (3-methyl-2-buten-1-ol), linalool, nerol and geraniol, and also farnesol (3,7,11-trimethyldodeca-2,6,10-trien-1-ol) and nerolidol (3,7,11-trimethyldodeca-1,6,10-trien-3-ol), in particular linalool, nerol and geraniol.

The process according to the invention is particularly advantageous when the reactant allyl alcohols used are geraniol and/or nerol, and the product allyl alcohol prepared is 2-linalool.

The reactant allyl alcohols may be used either starting from a precursor, directly without preceding purification and removal of any by-products present, or isolated and purified. For example, the hydrogenation of citral affords geraniol/nerol mixtures having a specific by-product spectrum, which has effects on the rearrangement to linalool.

The following by-products in geraniol/nerol in particular play an important role for the embodiment of the rearrangement:

Citronellol which is formed by overhydrogenation and, depending on the conversion of the hydrogenation, may be present in contents of 1–10% in the geraniol/nerol.

Trans- and cis-3,7-dimethyl-3,5-octadienol, which are referred to hereinbelow as isonerol 1 and isonerol 2, and are present in amounts of from 0.1 to 5% in the hydrogenation effluent.

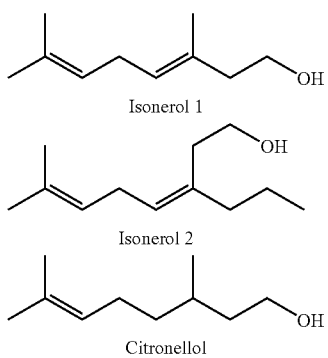

Isonerol 1

Isonerol 2

Citronellol

These three compounds can only be removed with great difficulty from geraniol and nerol with an acceptable level of complexity and expense, if at all. They therefore also have to be conducted into the rearrangement reaction, when the desire is to rearrange geraniol and/or nerol from the citral hydrogenation to linalool.

Suitable catalysts are, for example, those disclosed in DE 10046865.9 or in WO 00/142,177, or else dioxotungsten(VI) complexes of the general formula (III)

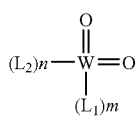

(III)

where $L_1$, $L_2$ are each independently a ligand selected from the group of amino alcohols, the amino phenols, or mixtures thereof, m, n are each 1 or 2.

For the performance of the isomerization, there are three process variants. The isomerization may be effected either in a reactor or in a battery of at least 3 reactors or in a reactive column (Lord reactor) which is equipped with reactor zones in the middle space, in order to achieve the required residence times.

An important fact for the embodiment of the rearrangement is that the rearrangement is an equilibrium reaction, and that, in the case of the isomerization of geraniol and/or nerol, the desired product, linalool, has a lower boiling point than geraniol and nerol, so that it may be removed from the equilibrium by distillation. This results in new linalool being constantly formed in the equilibrium reaction.

The process variants are described hereinbelow in a general manner using the example of the isomerization of geraniol and/or nerol to linalool.

When the process is carried out in a semicontinuous mode, geraniol or nerol or geraniol/nerol mixture is initially charged in a reactor having an attached distillation column. The catalyst is then metered in and distilling-off of linalool which is formed commences. At the same time, further geraniol or nerol or geraniol/nerol mixture is metered in, in order to keep the level in the reactor constant. During the process, further catalyst may also be added either continuously or discontinuously, in order to counteract partial deactivation of the catalyst.

When the starting geraniol and/or nerol mixtures used are the geraniol or nerol obtained directly from the citral hydrogenation, the by-products which have a higher boiling point than linalool accumulate in the course of the semibatch reaction in the reactor to an ever increasing extent. This of course results in an ever smaller fraction of the reactor volume being available for the desired reaction, the rearrangement of geraniol or nerol to linalool, which causes the linalool formation rate to decrease in the course of time.

When the linalool formation rate decreases to too great an extent as a result of by-products accumulated in the reactor, the metering of geraniol or nerol or geraniol/nerol mixture is stopped and further linalool is distilled off until virtually all of the geraniol and nerol still present in the reactor has been converted to linalool. At this time, the reactor contains, in addition to very small amounts of linalool, geraniol and nerol, the by-products mentioned, the catalyst and high boilers formed during the reaction. The citronellol, isonerol 1 and isonerol 2 by-products are now distilled off from the high boilers and the catalyst.

The bottoms remaining may either be disposed of, or, if the catalyst present therein is still sufficiently active, the bottoms may also be reused again in the next batch. The catalyst may also be removed from the bottoms, for example by crystallization, and the catalyst obtained in this way used again.

The citronellol, isonerol 1 and isonerol 2 by-products may thus be removed and subsequently isolated without losses of products of value and optionally fed to a further utilization.

When geraniol or nerol or geraniol/nerol mixtures which contain, only in a small amount, if any, of the citronellol, isonerol 1 and isonerol 2 by-products mentioned and also further by-products which can only be removed with difficulty from geraniol or nerol are used in the reaction, the period in which the feedstock is metered in and the linalool is distilled off may be distinctly extended because less by-products accumulate in the bottoms per unit time. It is recommended to meter in further catalyst, if the activity of the catalyst decreases to too great an extent as a result of deactivation.

It is also possible to dispense with the removal of the by-products at the end of the semibatch reaction.

The process is also very suitable for the rearrangement of geraniol or nerol or geraniol/nerol mixtures which contain other by-products which are difficult to remove from geraniol or nerol.

In the fully continuous process variant, catalyst and geraniol or nerol, or a mixture of geraniol and nerol, are simultaneously and continuously metered into a continuous reactor and linalool which is formed is continuously distilled off. In addition, high boilers are discharged by likewise continuously withdrawing a fractional amount of the reactor contents and removing the geraniol, nerol and linalool products of value still present in this fraction from high boilers formed during the reaction by distillation, for example by a simple evaporation or using a column. The involatile catalyst either remains in the high boilers which are fed to a disposal operation, or it may be precipitated from the high boilers by cooling, removed and reused again. The products of value which have been distilled off are recycled back into the reactor.

This process enables fully continuous rearrangement of geraniol or nerol, or mixtures of geraniol and nerol, to linalool, without the reaction having to be interrupted to discharge high boilers, or to add the catalyst.

Both the continuous and the semicontinuous process are carried out at temperatures of 130–220° C., preferably 150–200° C., either at atmospheric pressure or under reduced pressure. At reaction temperatures which are distinctly below the boiling point of linalool, it is recommended to carry out the reaction under reduced pressure, in order to enable linalool to be distilled out of the reactor.

The isomerization may also be effected in a plant composed of a plurality of reactors connected in series in a battery arrangement. The number of reactors used is generally between 2 and 10, preferably between 2 and 5, and particular preference is given to using 3 reactors.

In the first reactor, geraniol and/or nerol and also catalyst are metered in and partly isomerized at a pressure of from 60 to 1000 mbar and a temperature of from 150 to 200° C. This partly converted mixture is pumped into a second reactor in which full conversion is effected with regard to geraniol and nerol. The full conversion in the second reactor is enabled by the withdrawal of a vapor stream each from the first and the second reactor. The two vapor streams are combined and rectified in the column of the first reactor. The top product removed comprises linalool, low boilers and water, and geraniol/nerol are recycled into the first reactor. The 3rd reactor contains low boilers and catalyst and also in some cases citronellol and isonerol. Citronellol and isonerol are optionally removed together as the top product in the column of the third reactor. A continuous liquid stream is removed from the bottom of the third reactor and citronellol is removed together with isonerols from high boilers and catalyst in an evaporator. High boilers and catalyst are discarded; citronellol and isonerols from the evaporator are recycled into the bottom of the third reactor.

Suitable reactors in all processes are nonbackmixed reactors such as tubular reactors or delay time vessels equipped with internals, but preferably backmixed reactors such as stirred tanks, loop reactors, jet loop reactors or jet nozzle reactors. However, combinations of backmixed reactors and nonbackmixed reactors connected in series may also be used.

A plurality of reactors may optionally also be combined in a multistage apparatus. Such reactors are, for example, loop reactors having installed sieve trays, vessels in a battery, tubular reactors having intermediate feeding or stirred columns. It is recommended to equip all or some of the individual reactors with heat exchangers. In the reactors, good mixing of the reactants has to be ensured, which may be effected, for example, by stirring or pump circulation, optionally in combination with the treatment with static mixers or mixing nozzles.

The volume of the reactors should be such that the average residence time of the reaction mixture in the reactors is between 5 minutes and 8 hours, in particular between 10 minutes and 5 hours. With particular advantage, operation is effected with reactors which have about the same volume, although reactors having different volumes may in principle also be used.

The temperature in the reactors is generally between 150 and 200° C.

The pressure in the reactors is not critical, but should be sufficiently high that the contents of the reactors remain virtually fluid. This generally requires pressures of from 1 bar to 40 bar; the pressure is advantageously between 1 and 6 bar.

In a further process variant, the isomerization may be carried out in a distillation column equipped with Lord reactors (liquid space having mixing and only low pressure drop).

The Lord reactor features at least two chambers arranged one on top of the other in longitudinal direction, the chambers being separated from each other by liquid-tight trays, each chamber being connected to the chamber directly below by in each case one liquid overflow and a liquid product stream being removed from the lowermost chamber via the liquid overflow, the gas space above the liquid level in each chamber being connected to the chamber disposed directly above in each case by one or more directing tubes which each open into a gas distributor having orifices for the exit of gas below the liquid level, and also each having, around each gas distributor, at least one vertically aligned directing plate whose upper end ends below the liquid level and whose lower end ends above the liquid-tight tray of the chamber and which divides each chamber into one or more chambers having gas flow and one or more chambers having no gas flow.

The catalyst solution is introduced onto a column tray between upper separating section and reaction zone below it, which consists of a plurality of Lord reactors disposed one on top of the other.

Above the catalyst metering point is disclosed the separating section, within which a separation of the stream into linalool, low boilers and water, and also into geraniol, nerol and in some cases citronellol and isonerols. Below the catalyst metering point, the catalyst flows into the reaction zones. In the lowermost reaction chamber, i.e. just above the bottom, approximately all geraniol/nerol should have been consumed by isomerization. Any citronellols and isonerols present should be partly removed here by withdrawing a sidestream. A certain proportion of the bottom contents is conducted continuously through an evaporator. The nonevaporable high boilers are partly discarded together with catalyst from the bottoms and partly recycled to the fresh geraniol/nerol. The evaporable bottoms constituents from the evaporator consist predominantly, where present, of citronellol and isonerols and are recycled into the bottom.

The examples which follow describe the process according to the invention in detail, but without restricting it thereto:

Continuous Process

EXAMPLE 1

A 1.6 l stirred reactor having attached distillation column is initially charged with 825 g of geraniol/nerol mixture having a geraniol content of 69.5% and a nerol content of 29.5%, and is heated to 160° C., and a vacuum of 132–135 mbar is applied. A mixture of 5.14 g of an oxodiperoxotungsten solution (prepared by dissolving 1.29 g of tungstic acid in 3.86 g of 30% hydrogen peroxide at 40° C. over 6 h) and a solution of 2.63 g of 8-hydroxyquinoline in 26.3 g of methanol is then added. At the same time, the distilling-off via the distillation column of first the solvent of the catalyst and then linalool formed is commenced. To this end, the amount of linalool withdrawn via the top is controlled by the top temperature of the column using a reflux divider. At a top temperature of 133.8° C., 110 g of linalool per hour having a linalool content of about 98% are continuously distilled off. At the same time, under level control, about the same amount (112 g/h) of geraniol/nerol mixture and 1 g/h of a mixture of the above-described solutions of tungstic acid in 30% hydrogen peroxide and of 8-hydroxyquinoline in methanol are likewise continuously metered in. In addition, 110 g/h of the reaction mixture are likewise continuously freed of high boilers using a thin-film evaporator. The 107 g/h of the top effluent of the thin-film evaporator consists substantially of geraniol, nerol and linalool and is recycled back into the reactor. The bottom effluent of the thin-film evaporator (3 g/h) still contains small amounts of geraniol, nerol and linalool, and also high boilers formed in the reactor and a portion of the catalyst, and is discarded.

EXAMPLES 2 AND 3

The reaction was carried out in a fully analogous manner with pure geraniol and also with pure nerol as the feedstock, and identical results were obtained to those with the geraniol/nerol mixture as the feedstock.

Semicontinuous Process

EXAMPLE 4

A 1.6 l stirred reactor having attached a distillation column was initially charged with 800 g of geraniol/nerol mixture from the batchwise hydrogenation of citral and having a content of 72% geraniol, 21% nerol, 2% citronellol, 2% isonerol 1 and 1% isonerol 2, and heated to 160° C., and a vacuum of 132–135 mbar was applied. A mixture of 5.14 g of an oxodiperoxotungsten solution (prepared by dissolving 1.29 g of tungstic acid in 3.86 g of 30% hydrogen peroxide at 40° C. for 6 h) and a solution of 2.63 g of 8-hydroxyquinoline in 26.3 g of methanol was then added. At the same time, the distilling-off of first the solvent of the catalyst and then linalool formed was commenced. To this end, the amount of linalool withdrawn overhead was controlled by the top temperature of the column, which was kept in this experiment at 133.8° C., using a reflux divider. At the same time, under level control, about as much geraniol/nerol mixture of the abovementioned composition was likewise continuously metered in as linalool had been distilled off. The experimental duration until the metering-in was stopped was 79 h. In addition to the initially charged geraniol/nerol mixture, a further 6305 g of geraniol/nerol mixture were continuously metered in, and, after experimental duration of 30 h, the same amount of catalyst solution as described above was again metered in once. Once the metering of geraniol/nerol had been shut down, distillation was continued until no more linalool was distilled off. The total amount of linalool distilled off is 6570 g of 98% linalool. The vacuum was then reduced to 120–80 mbar and 289 g of a mixture was distilled off which contained 41% citronellol, 28% isonerol 1, 18% isonerol 2 and 4% linalool. After this distillation, 177 g of bottoms remained and were discarded.

EXAMPLES 5–8

The rearrangement of Example 1 was carried out in a similar manner with the following feedstocks:

EXAMPLE 5

Mixture of 45% geraniol, 50% nerol, 4% citronellol, 0.6% isonerol 1 and 2

EXAMPLE 6

Mixture of 96% geraniol, 0.2% nerol, 0.1% citronellol, 3.9% isonerol 1 and 2

EXAMPLE 7

99% geraniol

EXAMPLE 8

99% nerol

In Examples 7 and 8, the period in which the feedstock was metered in and the linalool was distilled off was doubled compared to Example 1 because less by-products per unit time accumulated in the bottom. After 80 h and after 115 h, catalyst was once again metered in. In addition, the removal of the by-products at the end of the semibatch reaction was dispensed with.

The invention claimed is:

1. A process for isomerizing reactant allyl alcohols of the general formula (I) to product allyl alcohols of the general formula (II)

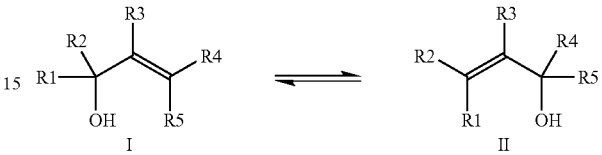

where R1 to R5 are each hydrogen or a mono- or polyunsaturated or saturated $C_1$–$C_{12}$-alkyl which may optionally be subtituted, wherein at least one reactant allyl alcohol or mixtures thereof is rearranged in semicontinuous mode to give the corresponding product allyl alcohol, by simultaneously metering in at least one reactant allyl alcohol or mixtures thereof into a catalyst-containing suitable reactor and wherein the catalyst used is one dioxotungsten(VI) complex or a mixture of different dioxotungsten(VI) complexes of the general formula III

where
  $L_1$, $L_2$ are each independently a ligand selected from the group of the amino alcohols, the amino phenols and mixtures thereof, and
  m, n are each the number 1 or 2.

2. A process as claimed in claim 1, wherein the product allyl alcohol formed is simultaneously distilled off.

3. A process as claimed in claim 1, wherein the reactant allyl alcohol used is geraniol, nerol or a mixture thereof.

4. A process as claimed in claim 3, wherein the geraniol and/or nerol are used directly from the citral hydrogenation.

5. A process as claimed in claim 3, wherein the geraniol/nerol has a citronellol content of from 1 to 10%.

6. A process as claimed in claim 3, wherein the geraniol/nerol has a trans- and cis-3,7-dimethyl-3,5-octadienol content from 0.1 to 5%.

7. A process as claimed in claim 1, wherein the isomerization takes place in a stirred tank.

8. A process as claimed in claim 1, wherein the isomerization takes place in a battery of reactors.

9. A process as claimed in claim 1, wherein the isomerization takes place in a reactive column (Lord reactor).

10. A process as claimed in claim 1, which is carried out at temperatures of from 130 to 220° C.

11. A process as claimed in claim 1, wherein the catalyst present in the by-products removed is isolated and optionally reused.

12. A process as claimed in claim 1, wherein $L_1$ and $L_2$ is 8-hydroxyquinoline.

* * * * *